(12) United States Patent
Boyer, II et al.

(10) Patent No.: US 9,463,051 B2
(45) Date of Patent: Oct. 11, 2016

(54) FACET JOINT PROSTHESIS

(71) Applicant: GLOBUS MEDICAL, INC., Audubon, PA (US)

(72) Inventors: Michael Lee Boyer, II, Phoenixville, PA (US); Daniel Laskowitz, Lancaster, PA (US); David C. Paul, Phoenixville, PA (US); William Rhoda, Media, PA (US); Andrew Iott, Newtown Square, PA (US); Andrew Lee, Santa Rosa, CA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 13/849,246

(22) Filed: Mar. 22, 2013

(65) Prior Publication Data

US 2014/0128925 A1 May 8, 2014

Related U.S. Application Data

(63) Continuation of application No. 11/634,242, filed on Dec. 6, 2006, now abandoned.

(60) Provisional application No. 60/742,527, filed on Dec. 5, 2005.

(51) Int. Cl.
*A61B 17/70* (2006.01)
*A61F 2/44* (2006.01)
*A61F 2/30* (2006.01)

(52) U.S. Cl.
CPC ....... *A61B 17/7059* (2013.01); *A61B 17/7064* (2013.01); *A61B 17/7067* (2013.01); *A61F 2/4405* (2013.01); *A61F 2002/305* (2013.01); *A61F 2002/3055* (2013.01); *A61F 2002/30331* (2013.01); *A61F 2002/30378* (2013.01); *A61F 2002/30462* (2013.01); *A61F 2002/30563* (2013.01); *A61F 2002/30565* (2013.01);
(Continued)

(58) Field of Classification Search
CPC .......... A61B 17/7065; A61B 17/7062; A61B 17/7064; A61F 2/4405
USPC ................ 606/247, 257, 325, 328
See application file for complete search history.

(56) References Cited

U.S. PATENT DOCUMENTS 4,204,284 A    5/1980  Koeneman
5,507,812 A *  4/1996  Moore .................. A61F 2/08
                                                 623/13.13

(Continued)

FOREIGN PATENT DOCUMENTS

| JP | 5649684 B2 | 1/2015 |
| WO | 2009003153 A2 | 12/2008 |
| WO | 2009006455 A1 | 1/2009 |

*Primary Examiner* — Eduardo C Robert
*Assistant Examiner* — Julianna N Harvey

(57) ABSTRACT

A facet joint prosthesis comprising an inferior prosthetic portion and a superior prosthetic portion is disclosed. Inferior prosthetic portion includes a first anchor member and a first articulating member and superior prosthetic portion includes a second anchor member and a second articulating member. The first articulating member comprises a support portion and first articulating surface and the second articulating member comprises a second articulating surface, and first and second articulating surfaces are configured and dimensioned to contact or engage one another. A flexible element is positioned between the support portion and the first articulating surface.

10 Claims, 19 Drawing Sheets

(52) U.S. Cl.
CPC ............... *A61F2002/30649* (2013.01); *A61F 2220/0025* (2013.01); *A61F 2220/0033* (2013.01); *A61F 2220/0075* (2013.01); *A61F 2310/00011* (2013.01); *A61F 2310/00179* (2013.01)

(56) References Cited

U.S. PATENT DOCUMENTS

| | | | |
|---|---|---|---|
| 5,571,191 A | 11/1996 | Fitz | |
| 5,755,796 A * | 5/1998 | Ibo | A61F 2/4425 606/247 |
| 5,993,486 A * | 11/1999 | Tomatsu | A61F 2/08 623/13.11 |
| 6,197,030 B1 * | 3/2001 | Pham | A61B 17/688 24/265 B |
| 6,579,319 B2 | 6/2003 | Goble et al. | |
| 6,811,567 B2 | 11/2004 | Reiley | |
| 8,460,341 B2 | 6/2013 | Chin et al. | |
| 2004/0236328 A1 | 11/2004 | Paul et al. | |
| 2005/0033434 A1 * | 2/2005 | Berry | 623/17.14 |
| 2005/0113927 A1 * | 5/2005 | Malek | 623/17.16 |
| 2005/0228385 A1 | 10/2005 | Iott et al. | |
| 2005/0245933 A1 * | 11/2005 | Sevrain | A61B 17/68 606/286 |
| 2006/0036252 A1 | 2/2006 | Baynham et al. | |
| 2006/0084987 A1 * | 4/2006 | Kim | A61B 17/70 606/258 |
| 2006/0155279 A1 * | 7/2006 | Ogilvie | 606/61 |
| 2006/0271054 A1 * | 11/2006 | Sucec | A61B 17/562 606/310 |
| 2013/0150897 A1 | 6/2013 | Bush | |

* cited by examiner

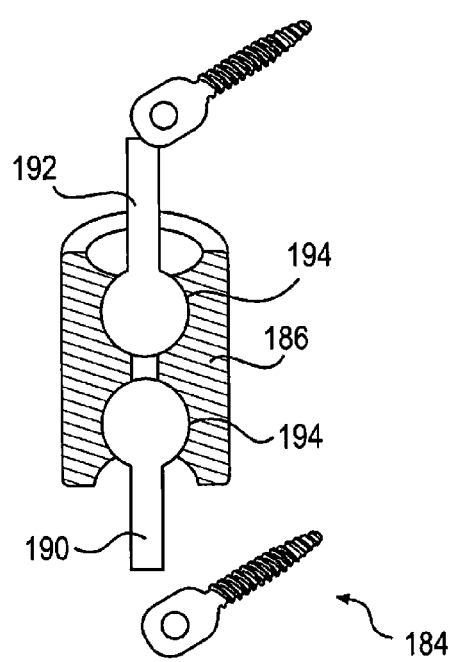
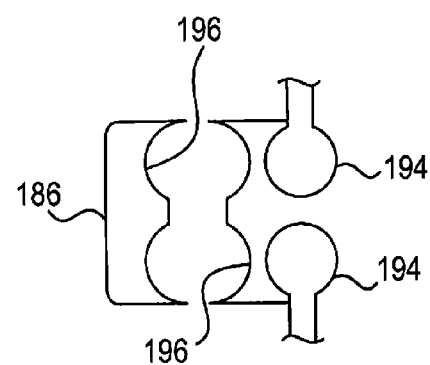
FIG. 16  FIG. 17

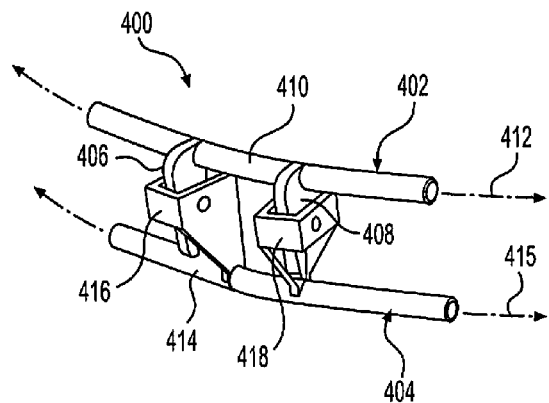
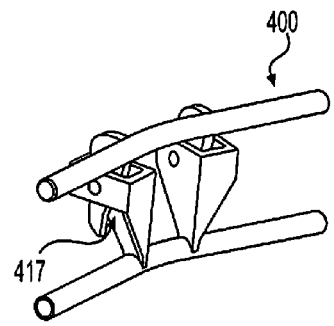
FIG. 27A  FIG. 27B
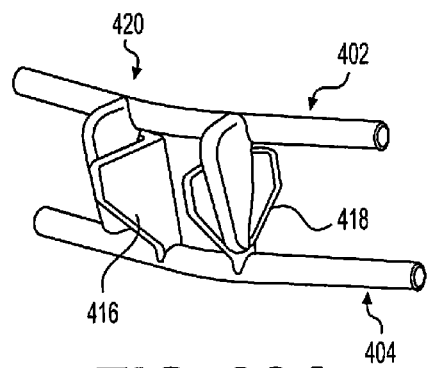
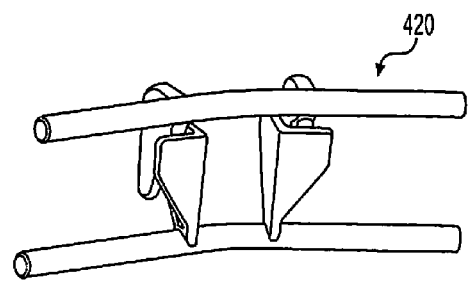
FIG. 28A  FIG. 28B
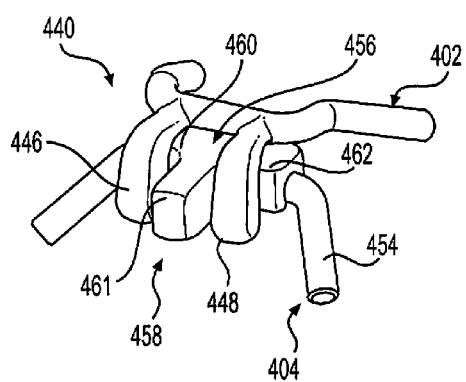
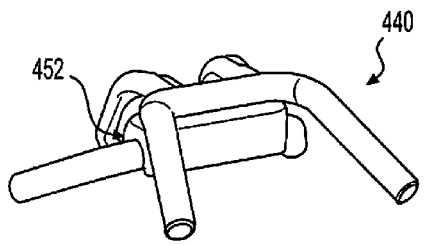
FIG. 29A  FIG. 29B

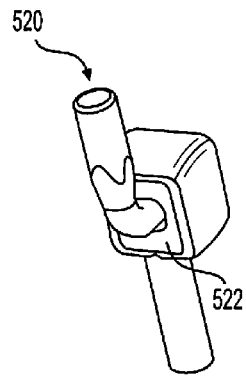 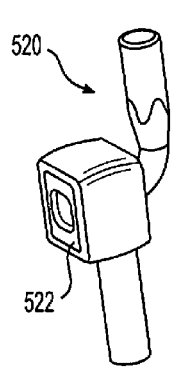 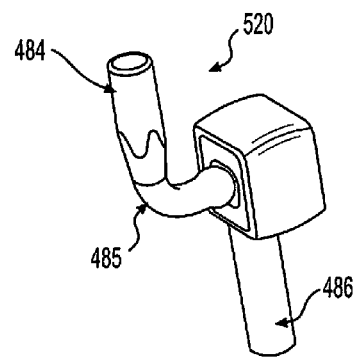
*FIG. 33A*    *FIG. 33B*    *FIG. 33C*
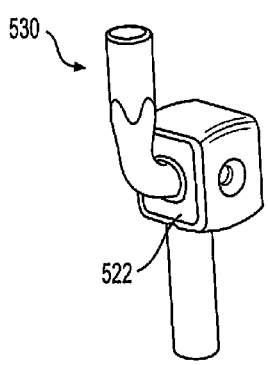 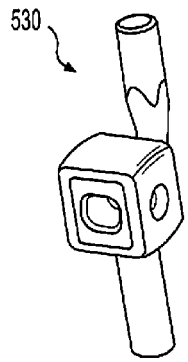 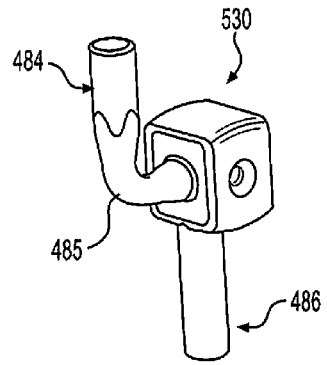
*FIG. 34A*    *FIG. 34B*    *FIG. 34C*

FACET JOINT PROSTHESIS

CROSS REFERENCE TO RELATED APPLICATIONS

This Patent Application is a continuation application claiming priority to U.S. patent application Ser. No. 11/634,242, filed Dec. 6, 2006, which claims priority to U.S. Provisional Application 60/742,527, filed Dec. 5, 2005, the entire contents of which are incorporated by reference.

FIELD OF THE INVENTION

The present invention generally relates to devices and methods for treating spinal stenosis or for alleviating pain or discomfort associated with the spinal column. More specifically, the present invention is directed to several different types of spinal joint replacement prostheses.

BACKGROUND OF THE INVENTION

The facet joints can deteriorate or otherwise become injured or diseased, causing lack of support for the spinal column, pain, and/or difficulty in movement.

Facet joint degeneration and disc degeneration frequently occur together, although one may be the primary problem and the other a secondary phenomenon due to altered mechanics of the spine. Central and lateral spinal stenosis, degenerative spondylolisthesis, and degenerative scoliosis may all result from the abnormal mechanical relationship between the anterior and posterior column structures of the spine resulting from such joint and/or disc degeneration.

Proper spinal motion requires normal function of both the disc and facet joints. Currently, surgical approaches for spinal stenosis do not restore normal function. In some instances, decompression with removal of soft tissue restraints and portions of the facet joints may actually cause instability, or, at a minimum, alter normal mechanics. As a result, instability that has inadvertently been induced by medical treatment can lead to further degeneration and pain Spinal fusion puts stress on adjacent structures, and accelerates transitional degeneration and may cause stenosis at the adjacent segment. Secondary operations for hardware removal are occasionally required, and bone graft donor site pain can be a real problem for many patients.

A facet joint replacement would allow spinal alignment and mobility to be preserved. Also, there would be less stress placed on adjacent levels, and normal anatomic structures (lamina, spinous process, ligaments) could be preserved. Therefore, a need exists for an improved facet joint prosthesis to provide an adjunct to anterior column disc replacement, or as a stand-alone treatment for patients with isolated posterior column disease.

SUMMARY OF THE INVENTION

Various facet joint prostheses are disclosed. In one embodiment, a facet joint prosthesis comprising an inferior prosthetic portion and a superior prosthetic portion is disclosed. Inferior prosthetic portion includes a first anchor member and a first articulating member and superior prosthetic portion includes a second anchor member and a second articulating member. The first articulating member comprises a support portion and first articulating surface and the second articulating member comprises a second articulating surface, and first and second articulating surfaces are configured and dimensioned to contact or engage one another. In one embodiment, a flexible element is positioned between the support portion and the first articulating surface.

In another aspect of the invention, a facet joint prosthesis having first prosthetic portion, second prosthetic portion, and a flexible element is disclosed. The first prosthetic portion includes a first anchor member and a first articulating member and the second prosthetic portion includes a second anchor member and a second articulating member. A flexible element is interconnected between the first and second articulating members.

BRIEF DESCRIPTION OF THE DRAWINGS

The invention will be more readily understood with reference to the embodiments thereof illustrated in the attached figures, in which:

FIG. 16 is a partial cross-sectional view of another embodiment of a facet joint prosthesis constructed according to the present invention;

FIG. 17 is an exploded view of the prosthesis of FIG. 16;

FIGS. 27A-27B are front and rear perspective views of another embodiment of a facet joint prosthesis constructed in accordance with the present invention;

FIGS. 28A-28B are front and rear perspective views of another embodiment of a facet joint prosthesis constructed in accordance with the present invention;

FIGS. 29A-29B are front and rear perspective views of another embodiment of a facet joint prosthesis constructed in accordance with the present invention;

FIGS. 33A-33C are front, rear, and front exploded perspective views, respectively, of another embodiment of a facet joint prosthesis constructed in accordance with the present invention; and FIGS. 34A-34C are front, rear, and front exploded perspective views, respectively, of another embodiment of a facet joint prosthesis constructed in accordance with the present invention

DETAILED DESCRIPTION OF THE PREFERRED EMBODIMENTS

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Figure 1:
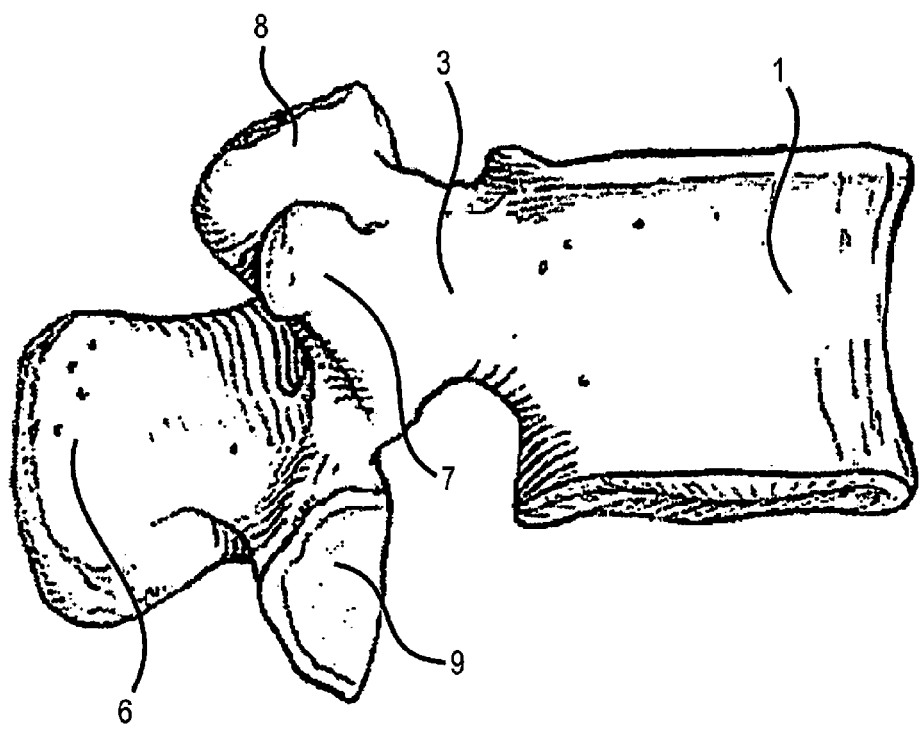
FIG. 1 is a lateral view of a representative vertebra.
Figure 2:
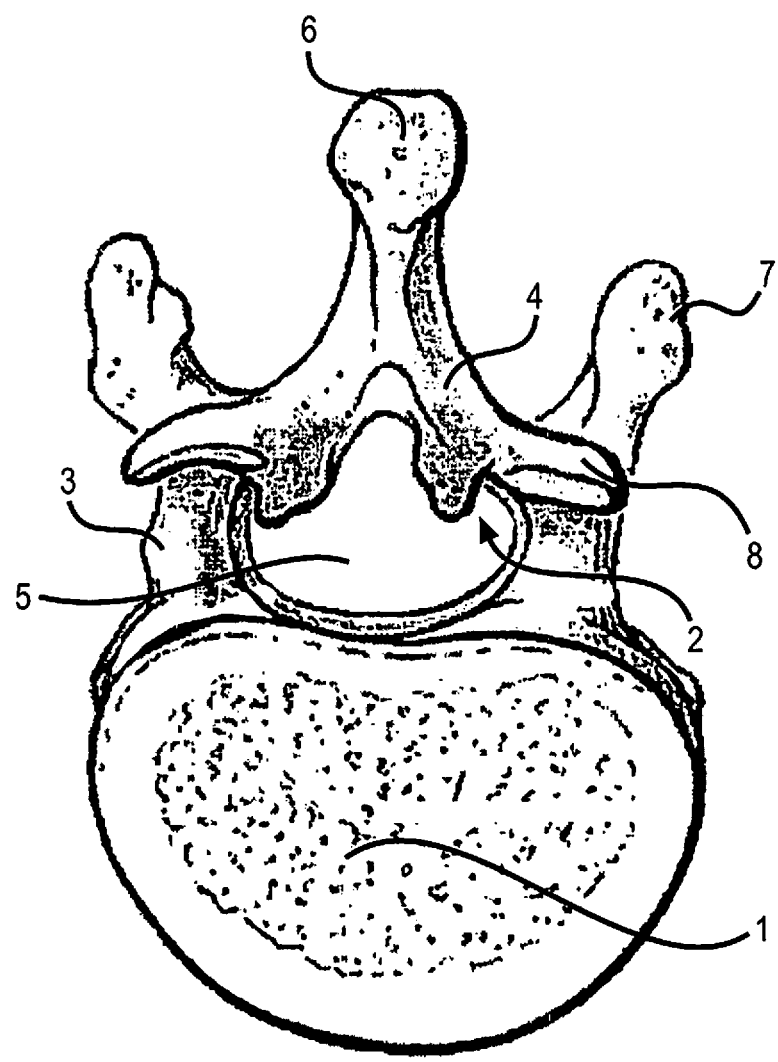
FIG. 2 is a superior view of the vertebra of FIG. 1.
Figure 3:
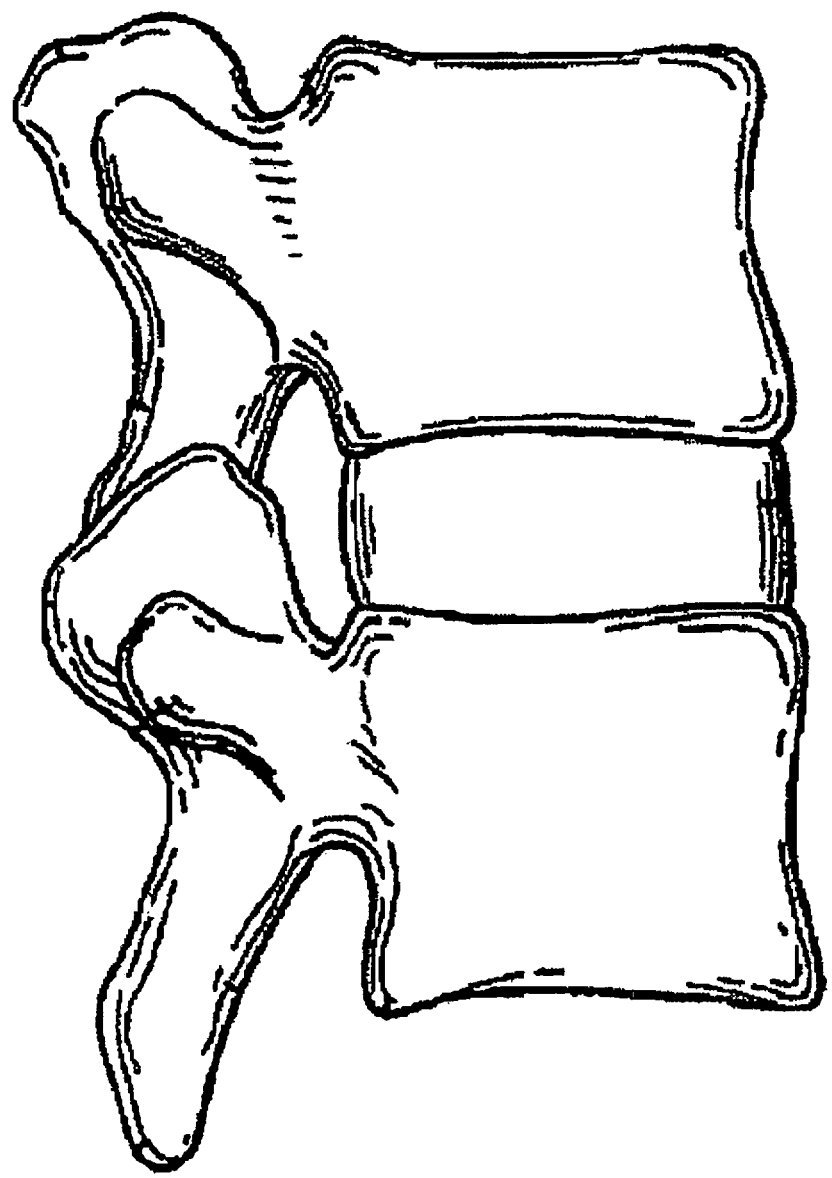
FIG. 3 is lateral view of a representative motion segment of the spine.

FIGS. 1 and 2 are lateral and axial views, respectively, of an exemplary vertebra of a vertebral column. Each vertebra includes a vertebral body 1, which is the anterior, massive part of bone that gives strength to the vertebral column and supports body weight. The vertebral arch 2 is posterior to the vertebral body 1 and is formed by the right and left pedicles 3 and lamina 4. The pedicles 3 are short, stout processes that join the vertebral arch 2 to the vertebral body 1. The pedicles 3 project posteriorly to meet two broad flat plates of bone, called the lamina 4. Together with the pedicles on the side and the vertebral body and discs in the front they form a canal, called the vertebral foramen 5, in the middle of the vertebrae through which the spinal cord and other structures pass.

Seven other processes arise from the vertebral arch. The spinous process 6 and two transverse 7 processes project from the vertebral arch 2 and afford attachments for back muscles, forming levers that help the muscles move the vertebrae. The remaining four processes, called articular processes, project superiorly from the vertebral arch (and are thus called the superior articular processes 8) and inferiorly from the vertebral arch (and are thus called the inferior articular processes 9). The superior and inferior articular processes 8 and 9 are in opposition with corresponding opposite processes of vertebrae superior and inferior adjacent to them, forming joints, called zygapophysial joints or, more regularly, the facet joints or facets. The facet joints permit gliding movement between the adjacent vertebrae. Facet joints are found between adjacent superior and inferior articular processes along the spinal column. Generally, a facet joint has a superior half and an inferior half. The superior half of the joint is formed by the vertebral level below the joint, and the inferior half of the joint is formed by the vertebral level above the joint. The facets have different orientations at different parts of the spine. This allows for different motions. For example the facet orientations at the lumbar spine primarily allow for flexion (forward bending) and extension (backward bending). Where as in the cervical spine the facets allow for flexion, extension, and a much larger amount of rotation, and side bending. The facets are surrounded by cartilage (joint capsule) that is innervated and capable of producing pain.

Figure 4:
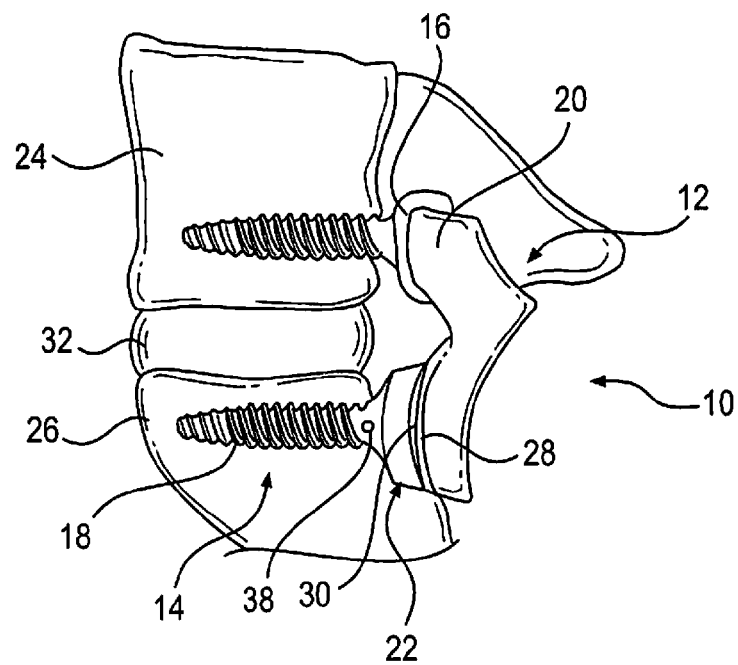
FIG. 4 is a lateral view of one embodiment of a facet joint prosthesis constructed in accordance with the present invention.
Figure 5:
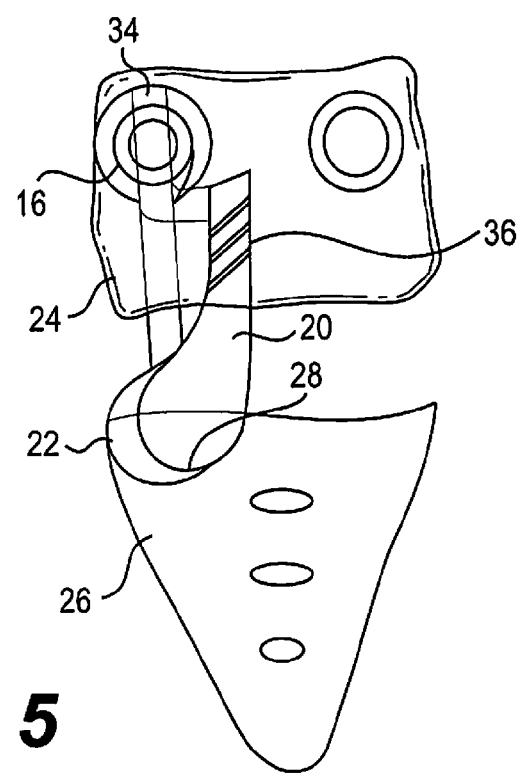
FIG. 5 is a dorsal view of the facet joint prosthesis of FIG. 4.

Referring to FIGS. 4 and 5, one exemplary embodiment of a facet joint prosthesis 10 according to the invention is shown. In general, prosthesis 10 comprises an inferior prosthetic segment, element, or portion 12 and a superior prosthetic segment, element, or portion 14. Segment or portion 12 is designated as "inferior" because it creates an artificial facet surface or portion in the inferior half of the facet joint. Similarly, segment or portion 14 is designated as "superior" because it creates an artificial facet surface or portion in the superior half of the facet joint. Similar nomenclature is used throughout this description, however, as an alternative to the "inferior" and "superior" nomenclature designation, "cephalad" and "caudal" may be used.

In one embodiment, prosthetic portions 12, 14 comprise an anchor member 16, 18 and an articulating member 20, 22, respectively. In this regard, inferior prosthetic segment 12 comprises a first or inferior anchor member 16 and a first or inferior articulating member 20. Similarly, superior prosthetic segment 14 comprises a second or superior anchor member 18 and a second or superior articulating member 22. Anchor members 16, 18 are configured and dimensioned to engage, anchor, or otherwise fix to a vertebra. Articulating members 20, 22 are configured and dimensioned to contact or engage adjacent articulating members such that the articulating members can move relative to one another, for example, by pivoting or by sliding towards, or away from, each other.

As shown in FIG. 4, the left inferior facet of superior vertebra 24 and left superior facet of inferior vertebra 26 have been resected and/or removed and prosthesis 10 has been attached to vertebrae 24, 26 to replicate the natural anatomy. Articulating member 20 of inferior prosthetic segment 12 engages articulating member 22 of superior prosthetic segment 14. In this regard, articulating member 20 comprises a generally convex articulating or bearing surface 28, and articulating member 22 comprises a generally concave articulating or bearing surface 30, and surfaces 28, 30 are configured and dimensioned to contact or engage one another, as described above. When the total facet joint is replaced, as shown in FIGS. 4-5, then surface 28 articulates with surface 30 to recreate the natural biomechanics of the spine motion segment made up of vertebra 24, vertebra 26, and intervertebral disc 32. In one embodiment, superior bearing surface 30 is sized to be larger than the articulating inferior bearing surface 28, to allow for motion of the joint. In alternate embodiments, alternative shapes and configurations of articulating surfaces 28, 30 may be utilized. For example, surface 30 may be any appropriate concave shape including, but not limited to, rectangular, disc shaped, trough shaped, or cup shaped, and inferior surface 28 may have a corresponding convex shape to mate, engage, or otherwise contact surface 30.

As best seen in FIG. 4, in one embodiment, first and second anchor members 16, 18 comprise bone screws. In one variation, the bone screws may be polyaxial screws. One type of polyaxial screw that may be used is disclosed in U.S. patent application Ser. No. 11/146,147, filed Jun. 7, 2005, the entire contents of which are incorporated by reference. In this regard the articulating members 20, 22, may include features to facilitate connection with the corresponding anchor or screw. In one exemplary embodiment, the articulating member 20 comprises a rod portion 34 configured and dimensioned to engage anchor 16. In this regard, a standard or typical pedicle screw may be utilized without modifying the connection means on the head of the screw, as pedicle screws are generally configured to accommodate a cylindrical or rod-like structure such as a spinal rod. As shown in FIG. 5, anchor or screw 16 may be implanted in a pedicle and articulating member 20 is sized and shaped to span the distance between a pedicle and an inferior articular process on the same side of a vertebral body. In one variation of articulating member 20, a flexible element 36 may be positioned between the anchor 16 and articulating surface 28. One type of flexible element that may be used is disclosed in U.S. patent application Ser. No. 10/762,533, filed Jan. 23, 2004, the entire contents of which are incorporated by reference. In alternate embodiments, a spring or other resilient or elastomeric element may be used.

Figure 23:
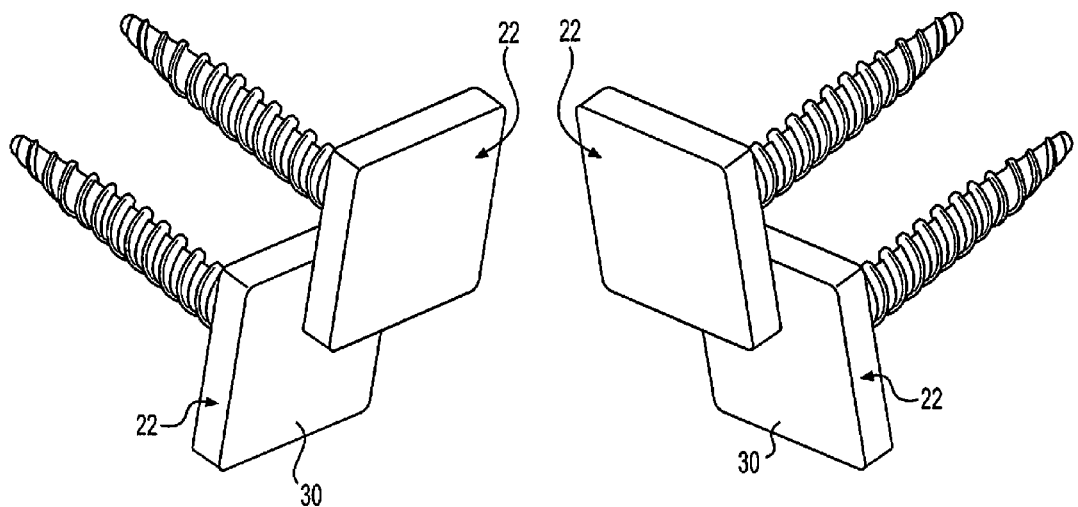
FIG. 23 is a perspective view of another embodiment of a facet joint prosthesis constructed in accordance with the present invention.

In another exemplary embodiment, articulating member 22 may comprise a modified screw cap or top configured to engage the screw head. In this regard, a standard or typical pedicle screw may be utilized with a modified cap. In another embodiment, superior articulating member 22 may comprise a connector portion 38 to allow lockable angulation and provide the optimum position of bearing surface 30. Referring to FIG. 23, in one embodiment articulating caps 22 may have a generally flat or plate like shape and include a bearing surface 30 to engage a similar adjacent cap. In the aforementioned embodiments, the superior articulating member may be positioned such that it has the appropriate cephalad and caudad directions as well as the appropriate medial/lateral angulation for the given level of the spine where the prosthetic is implanted.

The articulating members 20, 22 may be made of various materials commonly used in the prosthetic arts including, but not limited to, polyethylene, rubber, titanium, titanium alloys, chrome cobalt, surgical steel, or any other total joint replacement metal and/or ceramic, bony in-growth surface, sintered glass, artificial bone, any uncemented metal or ceramic surface, or combination thereof.

Figure 6:
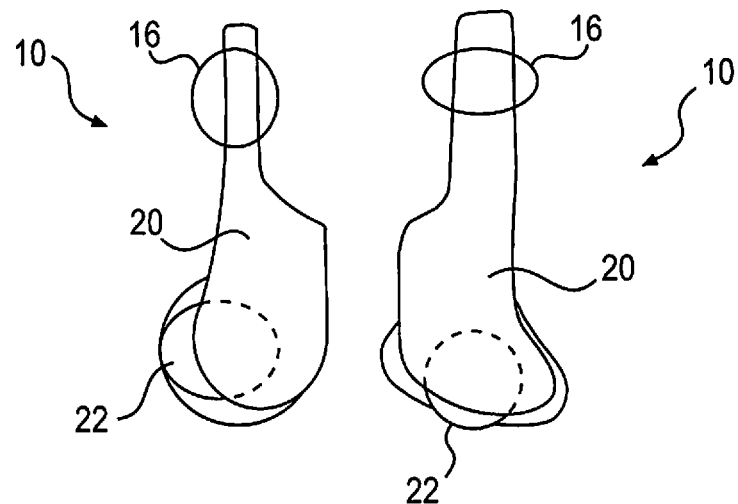
FIG. 6 is a dorsal view of another embodiment of a facet joint prosthesis constructed according to the invention.

In the embodiment of FIGS. 4-5, a prosthetic device 10 is shown wherein the inferior and/or superior halves of facet joints are replaced on one side of a given vertebra (unilateral). Those skilled in the art will appreciate that facet joints may be replaced on both sides of a given vertebra (bilateral) utilizing prosthetic device 10, as shown in FIG. 6, or a combination of each along a length of the spinal column.

Figure 7:
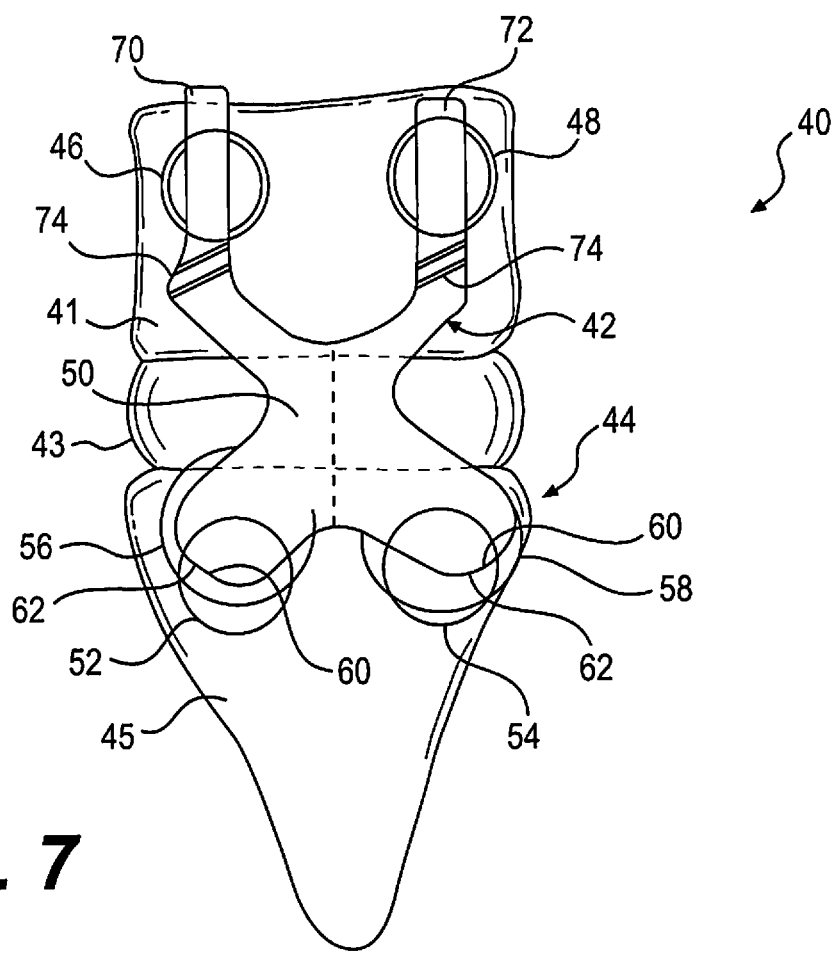
FIG. 7 is a dorsal view another embodiment of a facet joint prosthesis constructed in accordance with the present invention.

Referring to FIG. 7, another embodiment of a facet joint prosthesis 40 according to the invention is shown. In general, prosthesis 40 comprises a bilateral device and facet joints may be replaced on both sides of a given vertebra. Prosthesis 40 is similar to prosthesis 10 described above and generally comprises an inferior prosthetic segment 42 and a superior prosthetic segment 44. In this embodiment, inferior segment 42 comprises bilateral anchor members 46, 48 and a single bilateral articulating member 50. Articulating member 50 may be a single unitary piece or may comprise two or more separate pieces that may be assembled in-situ. Superior prosthetic segment generally comprises bilateral anchor members 52, 54 and bilateral articulating members 56, 58, similar to articulating member 22 described above with respect to FIGS. 4-5. Articulating member 50 comprises a pair of generally convex articulating or bearing surfaces 60 separated laterally on both sides of a given vertebra. Articulating members 56, 58 comprise generally concave articulating or bearing surfaces 62, and surfaces 60, 62 are configured and dimensioned to contact or engage one another, as described above. When the total facet joint is replaced, as shown in FIG. 7, then surfaces 60 articulate with surfaces 62 to recreate the natural biomechanics of the spine motion segment made up of vertebra 41, vertebra 43, and intervertebral disc 45.

In one exemplary embodiment, the articulating member 50 comprises bilateral rod portions 70, 72, each configured and dimensioned to engage an anchor, such as a pedicle screw, in a similar manner as described above with respect to prosthetic 10. Articulating member 50 is sized and shaped to span the distance between a pedicle and the inferior articular processes and provide space or an opening for the spinous process. In this regard, facet prosthesis 40 extends from its anchor point in a manner that does not require contact with, or mating to, the complex geometry of the lamina or posterior arch. Also, articulating member 50 is configured and dimensioned to be implanted without removal or resection of the spinous process. In one variation of articulating member 50, a flexible element 74 may be positioned between the anchors 46, 48 and articulating surfaces 60. One type of flexible element that may be used is disclosed in U.S. patent application Ser. No. 10/762,533, filed Jan. 23, 2004, the entire contents of which are incorporated by reference. In alternate embodiments, a spring or other resilient or elastomeric element may be used.

Figure 8:
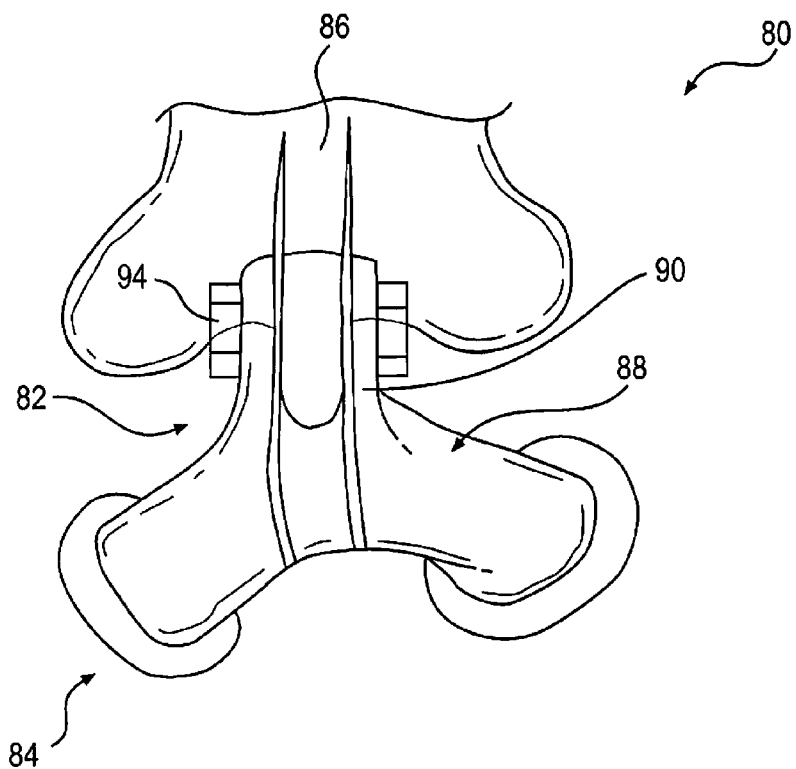
FIG. 8 is a dorsal view of another embodiment of a facet joint prosthesis constructed in accordance with the present invention.
Figure 9:
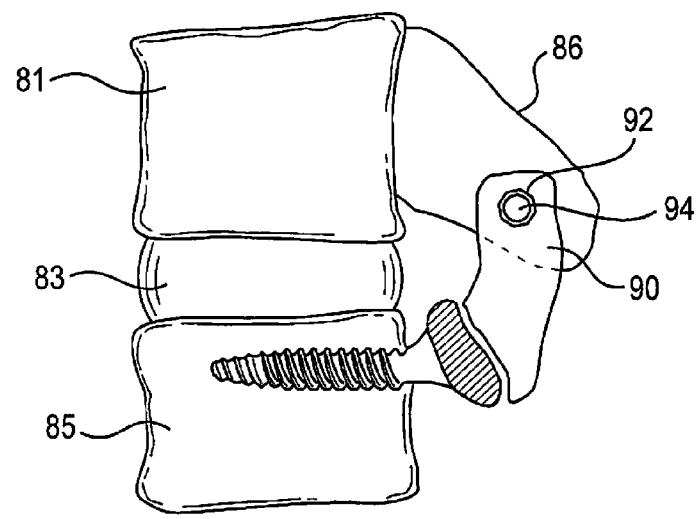
FIG. 9 is a lateral view of the prosthesis of FIG. 8.

Referring to FIGS. 8-9, another embodiment of a facet joint prosthesis 80 according to the invention is shown. In general, prosthesis 80 comprises a bilateral device to replace facet joints on both sides of a given vertebra. Prosthesis 80 is similar to prosthesis 40 described above, except inferior prosthetic segment 82 is configured to attach to the spinous process 86 on the superior vertebral body 81. In this regard, articulating member 88 of inferior segment 82 comprises a connecting portion 90 configured to contact, engage, or otherwise connect to spinous process 86. In one variation, shown in FIGS. 8 and 9, connecting portion 90 comprises a trough or H-shaped cross-section configured and dimensioned to extend upward from the underside of the spinous process 86 along either side of the spinous process. A slot or through-hole 92 extends laterally through connecting portion 90 to accommodate a trans-spinous fixation element 94, including, but not limited to, an anchor, pin, screw, or other device to fix articulating member 88 to spinous process 86. In all other respects, prosthesis 80 functions in a similar fashion as prosthesis 40 described above.

Figure 10:
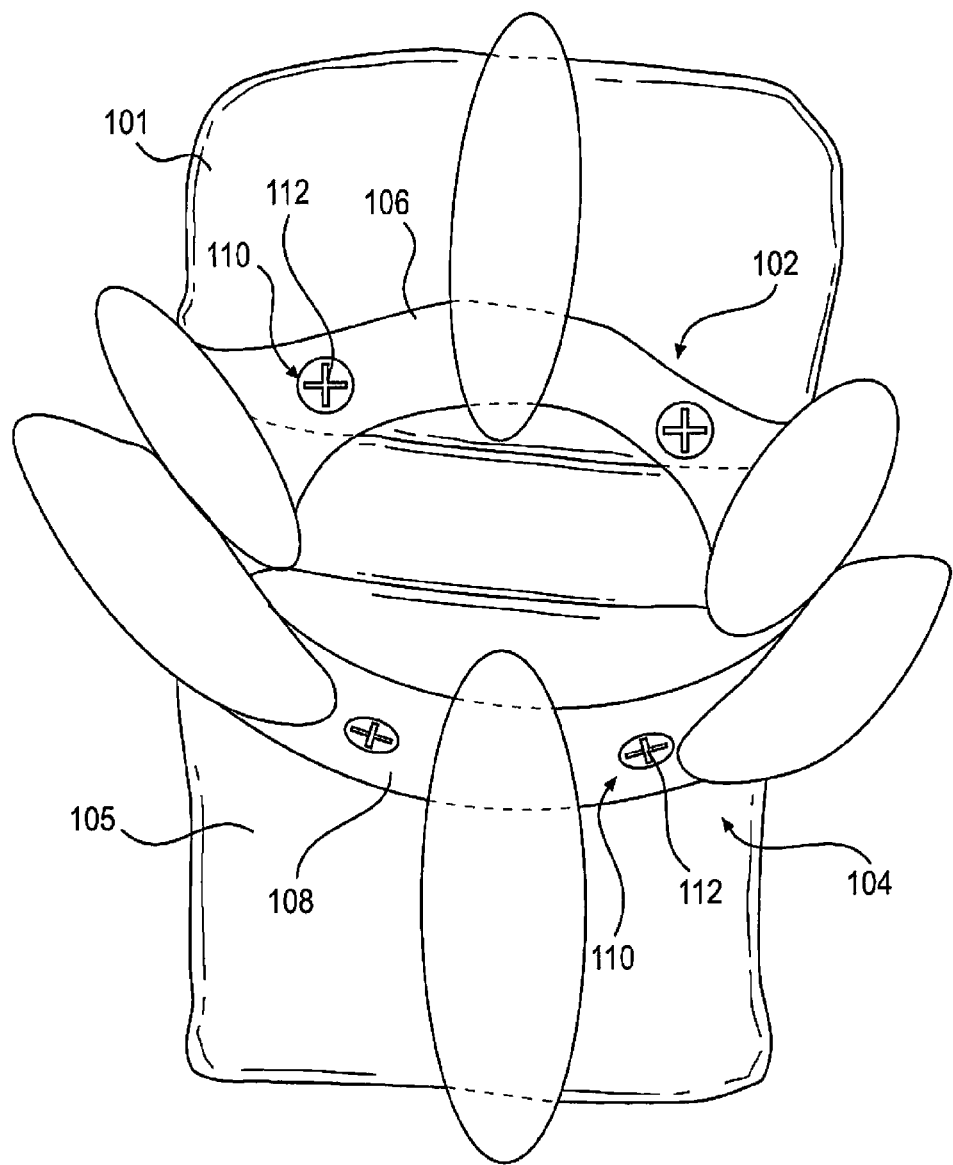
FIG. 10 is a dorsal view of another embodiment of a facet joint prosthesis constructed in accordance with the present invention.

Referring to FIG. 10, an alternate embodiment of a bilateral prosthesis 100 to replace facet joints on both sides of a given vertebra is shown. Prosthesis 100 is similar to prosthesis 40, 80 described above, except inferior prosthetic segment 102 and superior prosthetic segment 104 are configured to attach directly to the superior vertebral body 101 and inferior vertebral body 103, respectively, as opposed to the pedicles, or spinous process. In this regard, articulating member 106 of inferior segment 102, and articulating member 108 of superior segment 104 comprise one or more holes, slots, or openings 110 extending therethrough configured receive or accommodate one or fixation elements 112. Any type of fixation element 112 may be used, including, but not limited to, an anchor, pin, screw, staple or other device to fix articulating members 106, 108 to vertebral bodies 101, 103. In all other respects, prosthesis 100 functions in a similar fashion as prosthesis 40, 80 described above.

Figure 11:
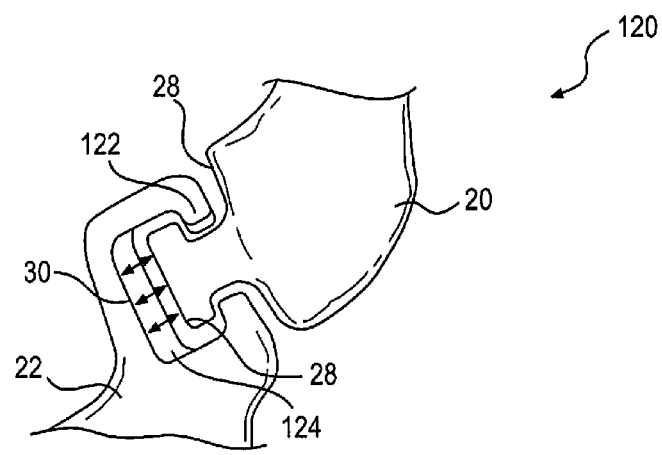
FIG. 11 is a partial cross-sectional view of another embodiment of a facet joint prosthesis constructed according to the present invention.

Referring to FIG. 11, an alternate embodiment of articulating surfaces 28, 30 of a facet joint prosthesis 120 is shown. In this embodiment, superior bearing surface 30 and inferior bearing surface 28 may be at least partially interlocked to provide constrained articulation. In this regard, superior bearing surface 30 may be grooved, cupped, or otherwise generally concave and may include capture arms 122 to at least partially enclose superior bearing surface 30 to define a general keyhole cavity. Inferior bearing surface 28 has a key shaped cross-sectional profile and is configured and dimensioned to be received or captured within the partially enclosed superior bearing surface 30 to provide "captured" or constrained articulation or movement. In that regard, when surface 28 engages surface 30, capture arms 122 are configured and dimensioned to extend inward about an indented profile portion of inferior surface 28 such that inferior articulating member 20 is captured within articulating member 22. The outer perimeter of inferior bearing surface 28 is smaller than the inner perimeter of the superior surface 30 such that inferior bearing surface 28 can move with respect superior bearing surface 30. In one variation, surfaces 28, 30 may directly contact each other, and in other embodiments, a polyethylene insert 124 may be interposed between the surfaces.

Figure 12:
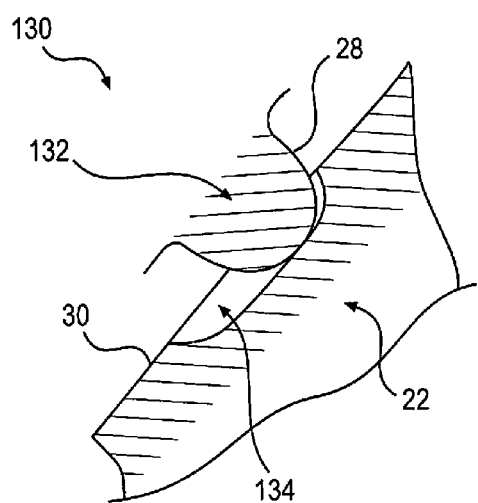
FIG. 12 is a partial cross-sectional view of another embodiment of a facet joint prosthesis constructed according to the present invention.
Figure 13:
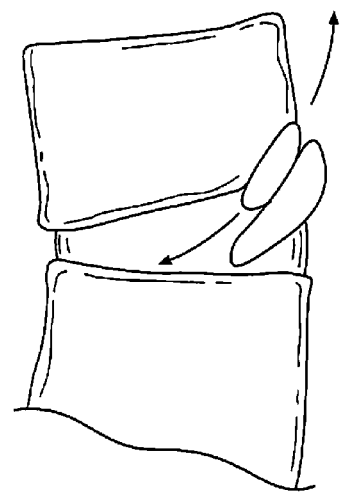
FIG. 13 is a lateral view of the prosthesis of FIG. 12.

Referring to FIGS. 12-13, an alternate embodiment of articulating surfaces 28, 30 of a facet joint prosthesis 130 is shown. In this embodiment, superior bearing surface 30 and inferior bearing surface 28 provide a protrusion 132 and track 134 configuration to provide at least partially constrained articulation.

Figure 14:
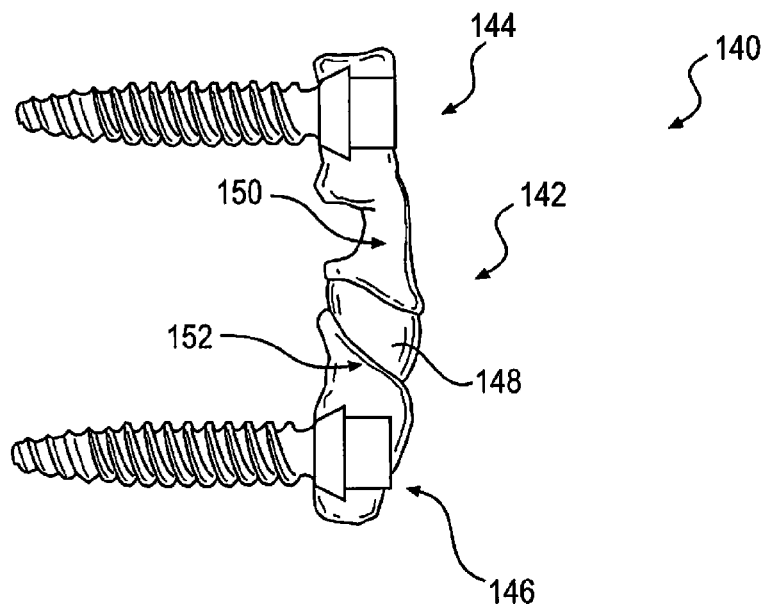
FIG. 14 is a lateral view of another embodiment of a facet joint prosthesis constructed according to the present invention.

Referring to FIG. 14, another embodiment of a prosthesis 140 is shown having an alternative joint interface 142. In this embodiment, inferior segment 144 and superior segment 146 of prosthetic 140 are joined or connected by a flexible member 148. Flexible member 148 comprises a soft material such as an elastomer or rubber that is attached to articulating members 150, 152 and may encapsulate the articulating surfaces. In operation, flexible member 148 of joint interface 142 provides constrained relative movement between articulating members 150, 152 as well as glide and cushioning ability to replicate the natural biomechanics of the spine.

Figure 15:
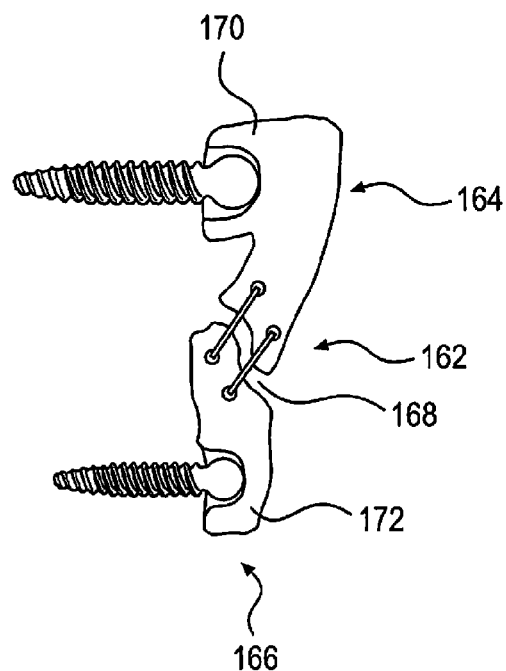
FIG. 15 is a lateral view of another embodiment of a facet joint prosthesis constructed according to the present invention.

Referring to FIG. 15, another embodiment of a facet joint prosthesis 160 is shown having an alternative joint interface 162. In this embodiment, inferior segment 164 and superior segment 166 of prosthetic 160 are joined or connected by linkages 168. In one embodiment, linkages 168 may comprise surgical cable, suture, elastomer or rubber bands, or any other suitable linkage. In operation, linkages 168 of joint interface 162 provide constrained relative movement between articulating members 170, 172 to replicate the natural biomechanics of the spine.

Referring to FIGS. 16-17, another embodiment of a facet joint prosthesis 180 is shown. In this embodiment, superior segment 182 and inferior segment 184 are inter-connected by a flexible sleeve 186. In one embodiment, sleeve 186 is made from an elastomer material. Superior and inferior segments 182, 184 comprise articulating members 190, 192 having a ball or spherical shaped head portion 194. Sleeve 186 has sockets 196 to accommodate head portions 194 and link articulating member 190 to articulating member 192. Sockets 196 permit rotational movement of articulating members 190, 192 with respect to the sleeve 186. Also, the resiliency of sleeve 186 permits distraction and compression between articulating members 190, 192. In operation, sleeve 186 provides constrained relative movement between articulating members 190, 192 as well as glide and cushioning ability to replicate the natural biomechanics of the spine.

Figure 18:
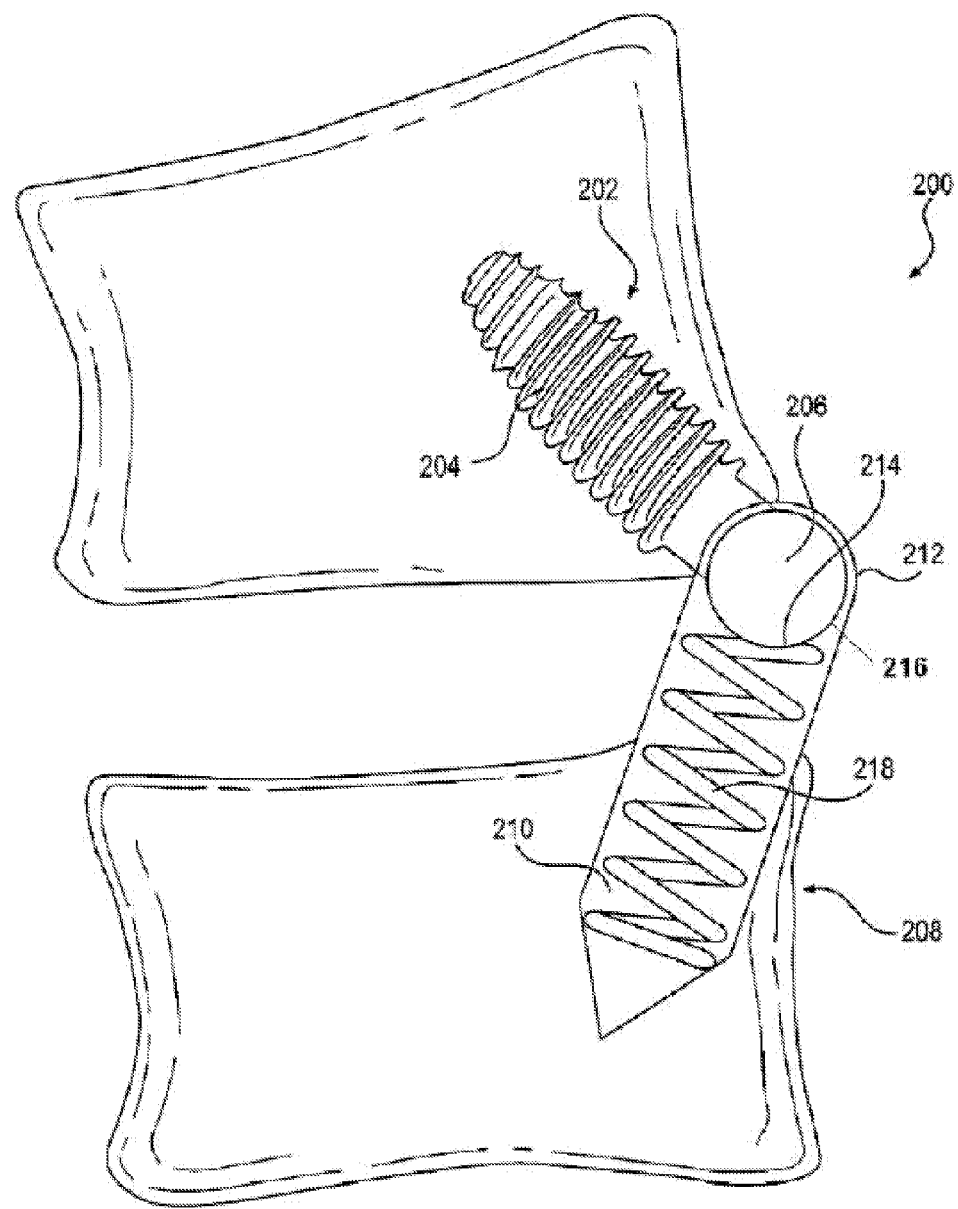
FIG. 18 is a lateral view of another embodiment of a facet joint prosthesis constructed according to the present invention.

Referring to FIG. 18, another embodiment of a facet joint prosthesis 200 is shown. In this embodiment, superior member 202 comprises an anchor portion 204 and an integrated articulating portion 206. Inferior member 208 comprises an anchor portion 210 and an integrated articulating portion 212. Articulating portion 206 comprises a ball or spherical shaped head member 214 and articulating portion 212 of inferior member 208 generally comprises a socket or slot 216 to receive head member 214 and link articulating portion 206 to articulating portion 212. Slot 216 permit rotational movement of articulating portion 206 with respect to articulating portion 212. A spring 218 may be housed within slot 216 to provide resiliency and allow distraction and compression between articulating portions 206, 212. In operation, slot 216 provides constrained relative movement between articulating portions 206, 212 as well as glide and cushioning ability to replicate the natural biomechanics of the spine.

Figure 19:
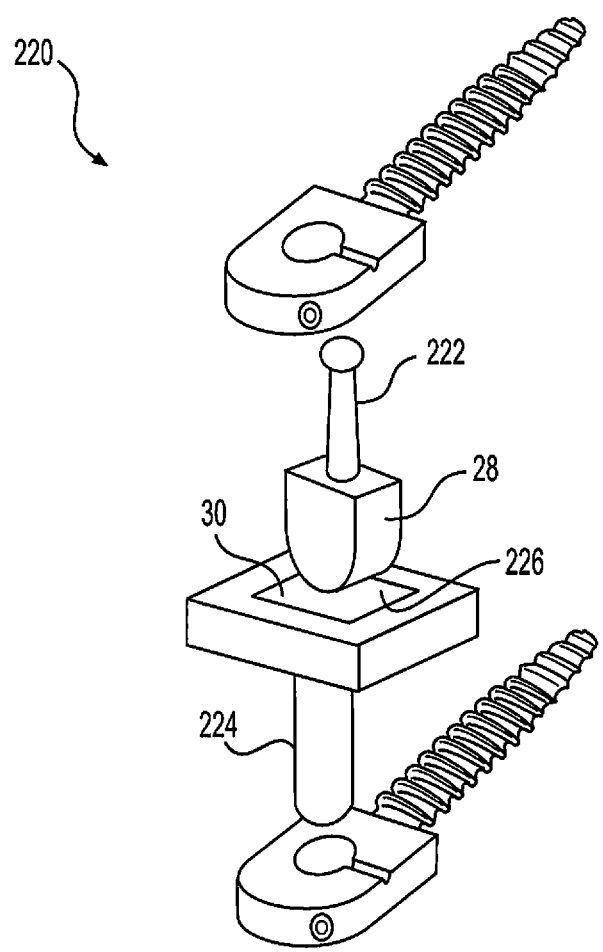
FIG. 19 is a partial exploded view of another embodiment of a facet joint prosthesis constructed in accordance with the present invention.

Referring to FIG. 19, another embodiment of a facet joint prosthesis 220 is shown including an alternate embodiment of articulating surfaces 28, 30. In this embodiment, superior bearing surface 30 comprises a cylindrical convex surface and inferior bearing surface 28 comprises a matching cylindrical concave surface to provide at least partially constrained articulation about one arcuate or cylindrical path in a single plane. Movement of inferior prosthetic member 222 about superior prosthetic member 224 in all other planes is constrained or limited by side walls 226 of superior surface 30. In one embodiment inferior and superior members 22, 224 are angularly lockable to adjust and/or the plane of action. In one variation, members 222, 224 may be locked post operatively via a percutaneous procedure.

Figure 20:
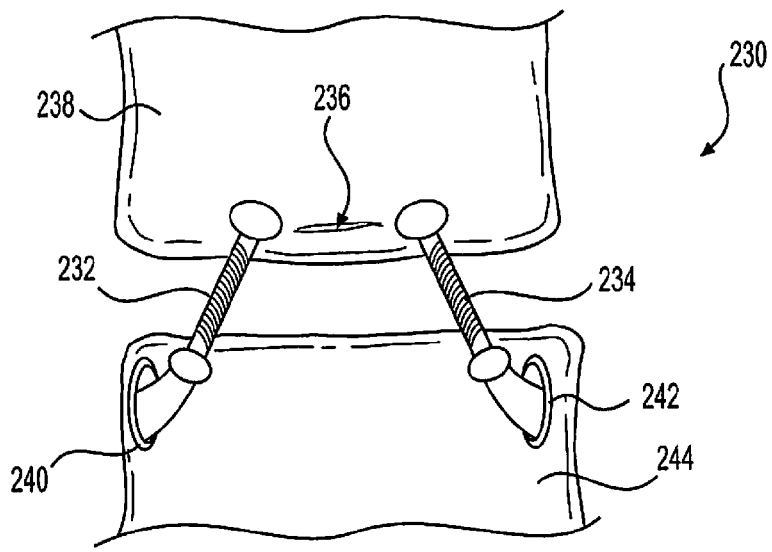
FIG. 20 is a dorsal view of a facet joint prosthesis constructed in accordance with the present invention.

Referring to FIG. 20, an alternate embodiment of a facet joint prosthesis 230 is shown. In this embodiment, cables 232, 234 may extend from a first anchor member 236 attached to the superior vertebra 238 to anchor members 240, 242 attached to the inferior vertebra 244. In one embodiment, first anchor member 236 comprises a pin extending through the spinous process or a ring or clip extending around the spinous process of vertebra 238. In another embodiment, anchor members 240, 242 comprise clips or rings extending about the transverse process of vertebra 244. Cables 232, 234 extend between anchor 236 to anchors 240, 242 to link the superior and inferior vertebral bodies to mimic the natural biomechanics of the spine.

Figure 21:
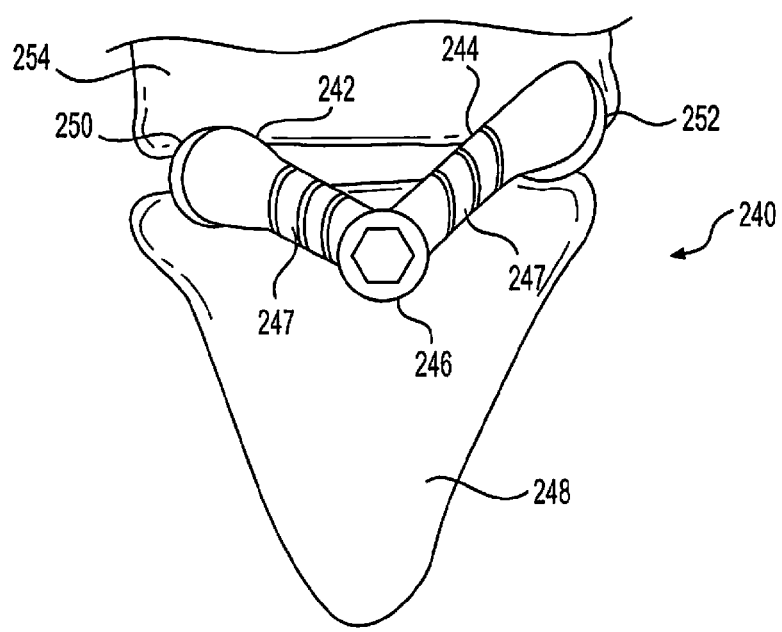
FIG. 21 is a dorsal view of another embodiment of a facet joint prosthesis constructed in accordance with the present invention.

Referring to FIG. 21, another embodiment of a facet joint prosthesis 240 is shown. In this embodiment, bilateral superior articulating members 242, 244 may be anchored to a vertebra or sacrum 248 to a central anchor 246. A pair of inferior articulating members 250, 252 may be anchored bilaterally on the superior vertebral body 254. Flexible elements 247 may be interposed between anchor 246 and articulating members 250, 252. Flexible elements 247 may be similar to the flexible elements 36 and 74 of previously described embodiments.

Figure 22:
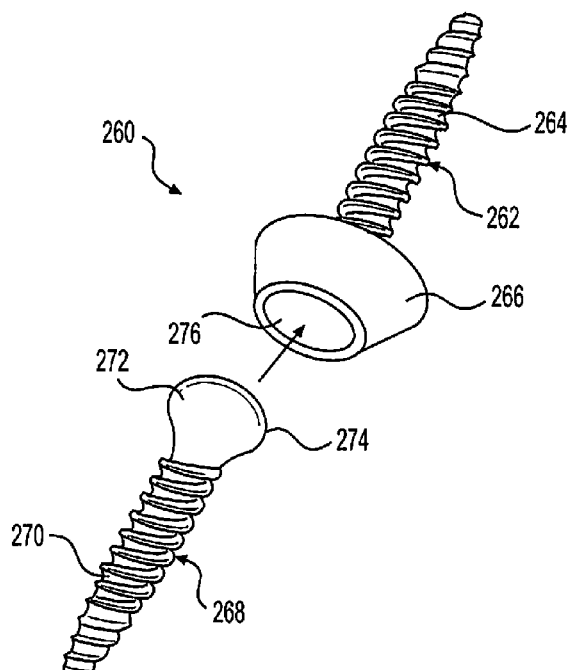
FIG. 22 is an exploded view of another embodiment of a facet joint prosthesis constructed in accordance with the present invention.

Referring to FIG. 22, another embodiment of a facet joint prosthesis 260 is shown. In this embodiment, superior member 262 comprises an anchor portion 264 and an integrated articulating portion 266. Inferior member 268 comprises an anchor portion 270 and an integrated articulating portion 272. Articulating portion 272 comprises a ball or spherical shaped head member 274 and articulating portion 266 of superior member 262 generally comprises a socket 276 to receive head member 274 and link articulating portion 266 to articulating portion 272. Socket 276 permits rotational movement of articulating portion 272 with respect to articulating portion 266. In operation, socket 276 provides constrained relative movement between articulating portions 266, 272 to replicate the natural biomechanics of the spine.

Figure 25:
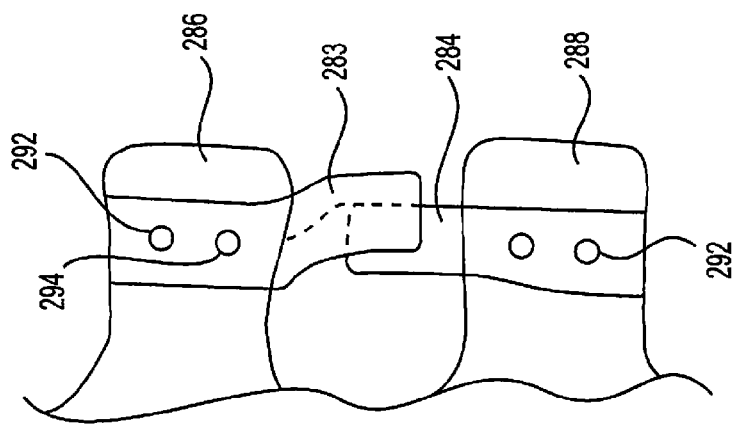
FIGS. 24-25 are views of another embodiment of a facet joint prosthesis constructed in accordance with the present invention.
Figure 24:
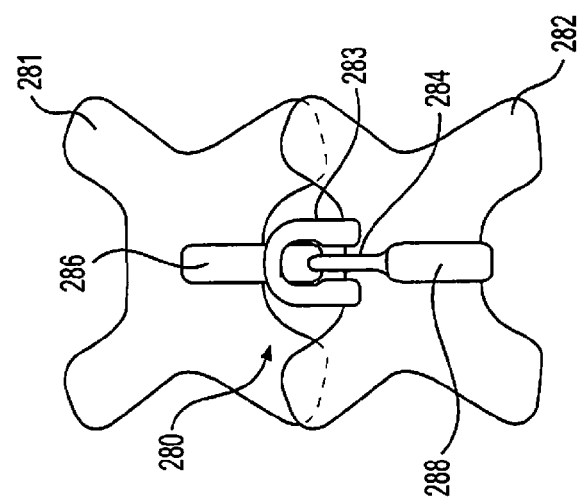

Referring to FIGS. 24-25, another embodiment of a facet joint prosthesis 280 according to the invention is shown. In general, prosthesis 280 comprises a device attached to the spinous processes of a motion segment to replace or replicate the facet joint(s) on one or both sides of a given vertebra. Prosthesis 280 generally comprises a straddle or yoke portion 283 configured to attach to the spinous processes 286 on the superior vertebral body 281 and a post or fin protrusion portion 284 configured to attach to the spinous processes 288 on the inferior vertebral body 282. As best seen in FIG. 24, yoke portion 283 comprises a trough or U-shaped cross-section configured and dimensioned to extend from the underside of the spinous process 286 along either side of the spinous process. Fin protrusion portion 284 comprises a straight cross-section configured and dimensioned to extend from the topside of the spinous process 288 and fit within the U-shaped cross-section of yoke portion 283. In this regard, fin protrusion 284 may articulate within yoke 283 to replicate the constrained movement of a natural facet joint. One or more slots or through-holes 292 may extend laterally through yoke portion 283 and fin portion 284 to accommodate a trans-spinous fixation element 294, including, but not limited to, an anchor, pin, screw, or other device to fix yoke portion 283 and fin portion 284 to spinous processes 286, 288 respectively.

Figure 26:
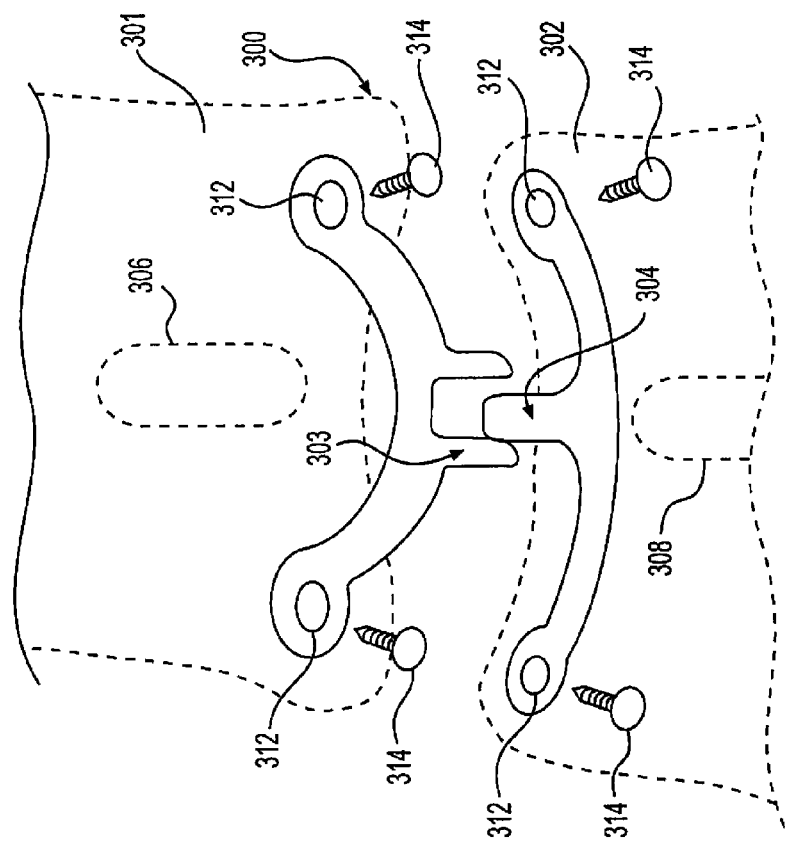
FIG. 26 is an exploded view of another embodiment of a facet joint prosthesis constructed in accordance with the present invention.

Referring to FIG. 26, another embodiment of a facet joint prosthesis 300 according to the invention is shown. In general, prosthesis 300 comprises a device that functions similar to prosthesis 280, described above, except that it is attached to the adjacent vertebral bodies of a motion segment by, for example, pedicle screws. Prosthesis 300 generally comprises a straddle or yoke portion 303 attached to a superior vertebral body 301 and a post or fin protrusion portion 304 on the inferior vertebral body 302. As best seen in FIG. 26, yoke portion 303 comprises a trough or U-shaped cross-section adjacent the underside of the spinous process 306. Fin protrusion portion 304 comprises a straight cross-section configured and dimensioned to extend adjacent the topside of the spinous process 308 and fit within the U-shaped cross-section of yoke portion 303. In this regard, fin protrusion 304 may articulate within yoke 303 to replicate the constrained movement of a natural facet joint. One or more slots or through-holes 312 may extend through yoke portion 303 and fin portion 304 to accommodate a fixation element 314, including, but not limited to, an anchor, pin, screw, or other device to fix yoke portion 303 and fin portion 304 to vertebral bodies 301, 302, respectively.

Referring to FIG. 27-29, alternative embodiments of facet joint prostheses 400, 420, and 440 according to the invention are shown. In general, prosthesis 400, 420 and 440 comprise bilateral devices and facet joints may be replaced on both sides of a given vertebra. Prostheses 400, 420 and 440 generally comprise an inferior prosthetic segment 402 and a superior prosthetic segment 404. According to one variation, inferior and superior segments 402, 404 may be attached to adjacent vertebral bodies respectively, to mimic the natural facet joints and the natural biomechanics of the spine.

Referring to the embodiment of FIGS. 27A-27B, inferior segment 402 of device 400 comprises a pair of bilateral articulating members 406, 408 extending in a downward or inferior direction from a lateral cross-member or support 410. Support 410 generally comprises a bar, rod, or other like structure, extending generally along a lateral axis 412. In one embodiment, articulating members 406, 408 generally comprise thin-walled straight, planar, plate-like members extending generally transverse to the axis 412 of support 410. Articulating members 406, 408 are generally spaced laterally a sufficient distance to be positioned on either side of the spinous process of the vertebral body to which the inferior segment 402 is attached. Articulating members 406, 408 are generally configured and dimensioned to fit within, interact with, or otherwise engage the superior articulating members 416, 418. In one embodiment, articulating members 406, 408 have a generally triangular shape with a ramped or angled surface or edge 417 along the anterior side thereof. The angled surface 417 generally tapers from a wider base portion at the top to a narrow tip at the bottom. One skilled in the art may appreciate, in operation such a ramped anterior facilitates a gliding or smooth movement rather than a dead stop, particularly in cases of forward translation.

Superior prosthetic segment 404 generally comprises a pair of bilateral articulating members 416, 418 extending in an upward or superior direction from a lateral support 414. Articulating members 416, 418 are generally spaced laterally a sufficient distance to be positioned on either side of the spinous process of the vertebral body to which the superior segment 404 is attached. Support 414 is similar to support 410 and generally comprises a bar, rod, or other like structure, extending generally along a lateral axis 415. In one variation, supports 410, 414 may comprise cylindrical rods which may be readily attached to the vertebral structure of a patient using known tools and techniques, including but not limited to, using pedicle screws and pedicle screw insertion techniques known to those skilled in the art. In one embodiment, shown in FIGS. 27A-27B, articulating members 416, 418 generally comprise a rectangular cup or socket-like structure, each configured and dimensioned for receiving an articulating member 406, 408. The interior or inner portion of articulating members 416, 418 generally comprise articulating or bearing surfaces configured to contact or engage articulating members 406, 408 to guide and limit motion of the superior and inferior prosthetic segments with respect to each other. In the embodiment of FIG. 27A-27B, the articulating members 416, 418 comprise rectangular wall members substantially surrounding articulating members 406, 408 laterally and posteriorly. In this regard, when device 400 is assembled or installed, articulating members 416, 418 generally limit or constrain rotation and lateral translation of the inferior segment 402 with respect to the superior segment 404. According to one variation, inferior and superior segments 402, 404 may be attached to adjacent vertebral bodies respectively to replace the facet joints and members 406, 408 may articulate with members 416, 418 to recreate the natural biomechanics of the spine motion segment. According to one embodiment, one or more through-holes 419 may extend through articulating members 416, 418 to accommodate a fixation element, including, but not limited to, an anchor, pin, screw, or other device to fix articulating members 406, 408 to articulating members 416, 418 and prevent relative movement between the inferior and superior segments 402, 404, respectively. As with previous embodiments, prosthetic 400 and inferior and superior segments 402, 404 may be made of various materials commonly used in the prosthetic arts including, but not limited to, polyethylene, rubber, titanium, titanium alloys, chrome cobalt, surgical steel, or any other total joint replacement metal and/or ceramic, bony in-growth surface, sintered glass, artificial bone, any uncemented metal or ceramic surface, or combination thereof. In one particular embodiment, inferior and superior segments 402, 404 may be made from a titanium or metal material and may include polyethylene bearing or mating surfaces.

Referring to FIGS. 28A-28B, another embodiment of a facet joint prosthesis 420 is shown. Prosthesis 420 is similar to prosthesis 400 except articulating members 416, 418 generally comprise a partial rectangular cup or socket-like structure. The interior or inner portion of articulating members 416, 418 generally comprise articulating or bearing surfaces configured to contact or engage articulating members 406, 408 to guide and limit motion of the superior and inferior prosthetic segments with respect to each other. In the embodiment of FIG. 28A-28B, the articulating members 416, 418 comprise partial rectangular wall members that are positioned to contact or engage articulating members 406, 408 along the medial lateral and anterior walls. In this regard, when device 420 is assembled or installed, articulating members 416, 418 is generally less limiting or constraining to extension and anterior-posterior translation of a patient's vertebrae and allows relative movement of the inferior segment 402 with respect to the superior segment 404.

Referring to FIGS. 29A-29B, another embodiment of a bilateral facet joint prosthesis 440 is shown. Inferior segment 402 of device 440 comprises a pair of bilateral articulating members 446, 448 extending in a downward or inferior direction from a lateral cross-member or support 450. In this embodiment, articulating members 446, 448 are generally hook shaped and comprise articulating or bearing surfaces 452 along the anterior side thereof. Articulating members 446, 448 are generally configured and dimensioned to fit around, interact with, or otherwise engage the superior articulating member 456.

Superior prosthetic segment 404 generally comprises a superior articulating member 456 extending from a lateral cross-member or support 454. Articulating member 456 generally comprises a T-shaped body 458 attached to support 454. Body 458 generally comprises articulating surfaces 460, 462 spaced laterally about a central posterior extending nose portion 461. Articulating surfaces 460, 462 are configured to contact or engage articulating or bearing surfaces 452 of members 446, 448 to guide and limit motion of the superior and inferior prosthetic segments 402, 404 with respect to each other. In this embodiment, when device 440 is assembled or installed, nose portion 461 is positioned to contact or engage articulating members 446, 448 along the inner lateral portion thereof and generally limit or constrain rotation and lateral translation of the inferior segment 402 with respect to the superior segment 404. According to one variation, inferior and superior segments 402, 404 may be attached to adjacent vertebral bodies respectively to replace the facet joints and members 446, 448 may articulate with member 456 to recreate the natural biomechanics of the spine motion segment. In this embodiment, articulating member 456 may be made from a polyethylene material.

Figure 30A:
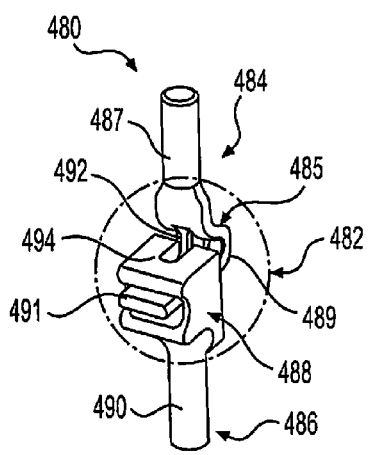
FIGS. 30A-30B are front and rear perspective views of another embodiment of a facet joint prosthesis constructed in accordance with the present invention.
Figure 30B:
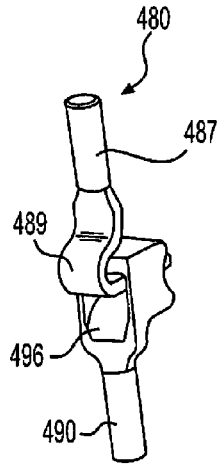

Referring to FIGS. 30A-30B, another embodiment of a facet joint prosthesis 480 is shown having an alternative articulating joint interface 482. In this embodiment, inferior segment 484 and superior segment 486 of prosthetic 480 are joined or connected by a hook/hinge configuration. The inferior segment 484 generally comprises a hook-like structure 485 extending from the end of a support portion 487. In one variation, support portion 487 may comprise a cylindrical structure such as a rod extending upward for screw attachment. Hook 485 generally comprises a curved portion 489 transitioning to a generally flat plate portion 491 and plate portion 491 is generally perpendicular to support portion 487. Superior segment 486 generally comprises a receiver member or head 488 extending from a support portion 490. In one variation, support portion 490 may comprise a cylindrical structure such as a rod extending downward for screw attachment. In one embodiment, head 488 generally comprises a hollow rectangular or box like structure that only has top, bottom and side walls, with no front or back wall. In operation, plate portion 491 fits into the hollow interior portion of receiver 488. In one embodiment, plate portion 491 may be strengthened by adding a gusset 492 that may mate into a cutout 494 in the top of receiver 488 when installed. As best seen in FIG. 30B, in another embodiment, a rounded transition portion 496 may be provided adjacent one of the posterior or anterior sides of receiver 488 to accommodate engagement with curved portion 489 of hook 485. In operation, hook 485 may rotate with respect to receiver 488 and curved portion 489 may contact or engage transition portion 496 to facilitate such rotational movement. According to one embodiment, when prosthesis 480 is installed, transition portion 496 and curved portion 489 may be positioned in a posterior facing orientation to facilitate articulation during flexion and extension of a patient's spine. As with previous embodiments, inferior and superior segments 484, 486 of prostheses 480, 510, and 520 may be made of various materials commonly used in the prosthetic arts including, but not limited to, polyethylene, rubber, titanium, titanium alloys, chrome cobalt, surgical steel, or any other total joint replacement metal and/or ceramic, bony in-growth surface, sintered glass, artificial bone, any uncemented metal or ceramic surface, or combination thereof. In one particular embodiment, inferior and superior segments 484, 486 may be made from a titanium or metal material.

Figure 31A:
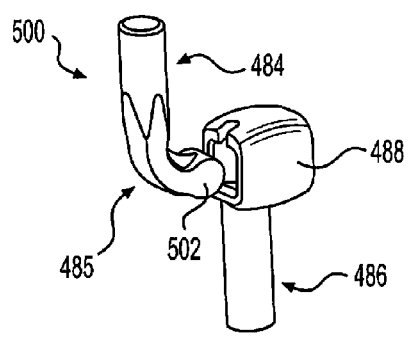
FIGS. 31A-31B are front and rear exploded perspective views of another embodiment of a facet joint prosthesis constructed in accordance with the present invention.
Figure 31B:
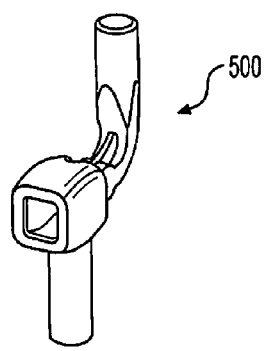

Referring to FIGS. 31-32, alternative embodiments of facet joint prostheses 500, 510 according to the invention are shown. Prostheses 500, 510 are similar to prosthesis 480 described above, except an alternative articulating joint interface 482 between the inferior and superior segments is provided. In one variation of prosthesis 500, shown in FIGS. 31A-31B, the distal end of hook 485 may be altered to include a generally cylindrical tip 502 instead of a flat plate portion 491. The interior of receiver 488 may have a generally matching or mating interior shape to accommodate tip 502 therein and facilitate constrained movement between the inferior and superior segments 484, 486. In operation, hook 485 may rotate or articulate with respect to receiver 488 and cylindrical tip 502 may contact or engage the cylindrically shaped interior to facilitate rotational movement in a single plane. According to one embodiment, when prosthesis 500 is installed, cylindrical portion may be orientated to facilitate articulation during flexion and extension of a patient's spine.

Figure 32A:
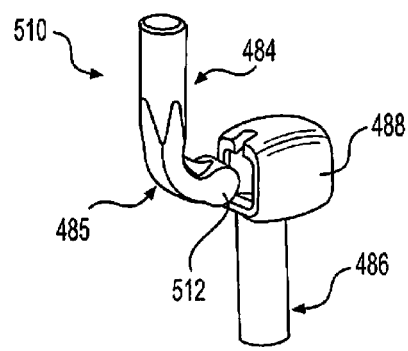
FIGS. 32A-32B are front and rear exploded perspective views of another embodiment of a facet joint prosthesis constructed in accordance with the present invention.
Figure 32B:
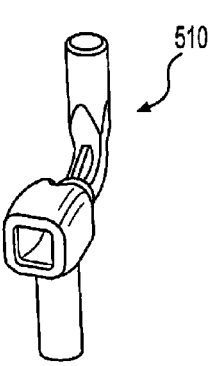

In another embodiment, shown in FIGS. 32A-32B, the distal end of hook 485 of prosthesis 510 may be altered to include a generally spherical tip 512. The interior of receiver 488 may have a generally matching or mating interior shape to accommodate tip 512 therein and facilitate constrained movement between the inferior and superior segments 484, 486. In operation, hook 485 may rotate or articulate with respect to receiver 488 and cylindrical tip 512 may contact or engage the spherically shaped interior to facilitate rotational or articulation movement in multiple planes. According to one embodiment, when prosthesis 510 is installed, the inferior and posterior segments 484, 486 may rotate or articulate during flexion, extension, or torsion of a patient's spine.

In another embodiment, shown in FIGS. 33-34, alternative embodiments of facet joint prostheses 520, 530 according to the invention are shown. Prostheses 520, 530 are similar to prosthesis 510 described above, except an alternative articulating joint interface 482 between the inferior and superior segments is provided. In general, prostheses 520, 530 may include a sleeve or insert member 522 inserted into the inner of receiver 488 and generally interposed between the hook member 485 and receiver 488. In one embodiment, insert member 522 may be made from a polyethylene material to provide altered or enhanced wear characteristics as compared to metal on metal contact. In yet another embodiment, insert member 522 may be made from a polyurethane or other like flexible material to provide a cushioning or a dampening characteristic to the articulating joint. In one variation of prosthesis 530, shown in FIGS. 34A-34C, insert member 522 may be screwed into the interior portion of receiver 488. In another embodiment of a prosthesis 520, the interior of receiver 488 may have an insert member 522 slidably or snapped into the interior portion of receiver 488. Insert member 522 generally encapsulates the distal tip of hook 485 having an interior shape to accommodate and/or mate the distal tip and to facilitate constrained movement between the inferior and superior segments 484, 486. In operation, hook 485 may contact or engage insert 522 and the distal tip may articulate or rotate with respect thereto.

While the invention herein disclosed has been described by means of specific embodiments and applications thereof, numerous modifications and variations can be made thereto by those skilled in the art without departing from the scope of the invention.

What is claimed is:

1. A spinal implant comprising:
   a superior member comprising a first anchor portion and a first articulating portion; and
   an inferior member comprising a second anchor portion and a second articulating portion;
   wherein the first articulating portion comprises a ball and the second articulating portion comprises a socket to receive the ball, wherein the first articulating portion is capable of articulating with respect to the second articulating portion,
   wherein the inferior member having a length extending from a distal-most end to a proximal-most end and comprises a spring that is housed within a slot positioned inside the inferior member, the spring extending greater than half the length of the inferior member, and
   wherein the first anchor portion and the first articulating portion are configured to be a unitary piece of the superior member.

2. The spinal implant of claim 1, wherein the implant comprises a facet joint prosthesis.

3. The spinal implant of claim 1, wherein at least one of the superior member and the inferior member are formed of titanium.

4. The spinal implant of claim 1, wherein at least one of the superior member and the inferior member are formed of polyethylene.

5. The spinal implant of claim 1, wherein the inferior member has a longitudinal axis extending along its length, and the second anchor portion extends along the longitudinal axis of the inferior member.

6. The spinal implant of claim 1, wherein the superior member has a length extending from a distal-most end to a proximal-most end, the superior member has a longitudinal axis extending along its length, and the first anchor portion extends along the longitudinal axis of the superior member.

7. The spinal implant of claim 1, wherein the superior member has a threaded portion along the first anchor portion.

8. The spinal implant of claim 1, wherein the second anchor portion is integral with the second articulating portion of the inferior member.

9. The spinal implant of claim 1, wherein the spring extends from the second articulating portion into the second anchor portion.

10. A spinal implant comprising:
    a superior member comprising a first anchor portion and a first articulating portion; and
    an inferior member comprising a second anchor portion and a second articulating portion, wherein the inferior member includes a spring member housed therein;
    wherein the first articulating portion is capable of articulating with respect to the second articulating portion,
    wherein the first articulating portion comprises a spherical shaped head member and the second articulating portion comprises a slot for receiving the spherical shaped head member,
    wherein the inferior member includes a length extending from a distal-most end to a proximal-most end and the spring member is positioned inside the inferior member and extends greater than half the length of the inferior member and
    wherein the first anchor portion and the first articulating portion are configured to be a unitary piece of the superior member.

* * * * *